United States Patent [19]

Johnson

[11] Patent Number: 5,089,503

[45] Date of Patent: Feb. 18, 1992

[54] TEMPERATURE STABLE 5-FLUOROURACIL COMPOSITIONS

[75] Inventor: James B. Johnson, Upper Montclair, N.J.

[73] Assignee: Hoffmann-La Roche Inc., Nutley, N.J.

[21] Appl. No.: 409,852

[22] Filed: Sep. 20, 1989

Related U.S. Application Data

[63] Continuation of Ser. No. 57,149, Jun. 3, 1987, abandoned.

[51] Int. Cl.$^5$ .............................. A61K 31/505
[52] U.S. Cl. .................... 514/274; 514/970
[58] Field of Search ................ 514/274, 970

[56] References Cited

U.S. PATENT DOCUMENTS

| | | | |
|---|---|---|---|
| 2,802,005 | 8/1957 | Heidelberger et al. | 544/313 |
| 2,885,396 | 5/1959 | Heidelberger et al. | 536/23 |
| 4,253,580 | 3/1981 | Doi et al. | 215/228 |
| 4,484,920 | 11/1984 | Kaufman et al. | 604/416 |
| 4,488,656 | 12/1984 | Fukuoka et al. | 215/307 |

FOREIGN PATENT DOCUMENTS

83948W/51 8/1975 Japan.

OTHER PUBLICATIONS

Pharmacopeial Forum, p. 194, Mar.–Apr. 1985, The United States Pharmacopeial Convention.
The United States Pharmacopeia, USP XXI, Supplement 3, Nov. 1, 1985, The United States Pharmacopeial Convention.
Benvenuto, John A. et al. Am. J. Hospital Pharmacy 38:1914–8 (1981).
Quebbman, Edward J. et al. Am. J. Hospital Pharmacy 41:1153–5 (1984).
Physician's Desk Reference, Pub. by Charles Baker, pp. 1499–1500 (1981).

*Primary Examiner*—Glennon H. Hollrah
*Assistant Examiner*—Gary E. Hollinden
*Attorney, Agent, or Firm*—George M. Gould; George W. Johnston; Alan P. Kass

[57] ABSTRACT

Temperature stable 5-fluorouracil compositions are disclosed. A solution of 5-fluorouracil and a base forms the composition. The pH of the composition is about 9.1 to about 9.3. The composition is less prone to precipitate at temperatures below 60° F.

7 Claims, No Drawings

TEMPERATURE STABLE 5-FLUOROURACIL COMPOSITIONS

This is a continuation of application Ser. No. 07/057,149 filed June 3, 1987 now abn.

BACKGROUND OF THE INVENTION

5-Fluorouracil (5 FU) is a fluorinated pyrimidine exhibiting antimetabolite activity and is a known antineoplastic agent.

5FU has long been used as a drug for the palliative management of various carcinomas including carcinoma of the colon, rectum, breast, stomach, and pancreas. It is frequently used in patients who are considered incurable by surgery or other means.

This compound is thought to interfere with the synthesis of DNA and to a lesser extent inhibits the formation of RNA. Since DNA and RNA are essential for cell growth and division, the effect of 5FU may be to create a thymine deficiency which provokes unbalanced growth and death of the cell. The effects of DNA and RNA deprivation are most marked on cells such as carcinoma cells which grow most rapidly.

5FU is an article of commerce and is generally supplied for intravenous injection in 10 ml. ampuls at a concentration of 50 mg/ml. The current 5FU formulations are colorless to faint yellow aqueous solutions which are at a pH of about 8.8. The current fluorouracil formulations are also temperature sensitive and must be stored at a temperature of above about 60° F. in order to avoid precipitation. Often, during shipment of the drug from, supplier to user they are exposed to temperatures below this range. The ampuls may arrive at their destination with the 5FU precipitated into large agglomerates which render the product unsuitable for use in that form.

The precipitate formation at low temperatures during winter shipment is a statistical phenomenon and occurs frequently. The precipitation yields large initial heterogenous nucleation at a few sites, and subsequent secondary growth. This necessitates the inconvenience of resolubilizing by heating to 140° F. with vigorous shaking. The solution must then slowly be cooled to body temperature before administration.

Heretofore, it has not been possible to distribute a 5FU formulation in a sealed container suitable for administering an injectable unit dose where the contents do not precipitate upon exposure to the low temperatures which often occur during shipment. With vial formulations precipitation at lower temperatures is particularly problematic, and may occur at temperatures and conditions where the corresponding ampul formulations would remain stable.

Accordingly, there has long been a need for a stable 5FU formulation suitable for storage in a sealed container suitable for administering an injectable unit dose where the contents do not precipitate at the temperatures below about 60° F. which often occur during shipment.

SUMMARY OF THE INVENTION

The instant invention comprises a composition of 5FU which remains stable at temperatures down to 32° F. when stored in a sealed container suitable for administering an injectable unit dose.

The instant invention also comprises a method for the manufacture of a 5FU composition which remains stable down to a temperature of 32° F. when stored in a sealed container suitable for administering an injectable unit dose.

DETAILED DESCRIPTION

The 5FU composition of the instant invention comprises a solution of 5FU and a base. The 5FU solution is manufactured according to current production methods known to one skilled in the art. Base is added so that the pH of the final composition is greater than 9 and less than 9.4.

Particularly preferred is a 5FU solution manufactured according to current production methods to which sodium hydroxide base has been added so that the pH of the final composition is about 9.1 to 9.3 and the concentration of 5FU is 50 mg/ml.

Although the pH range of the composition may vary between greater than 9 up to 9.4, as the pH of the composition increases the 5FU itself begins to lose activity. Hence it is most desirable to keep the pH of the composition between 9.1 to 9.3.

This composition will remain stable down to 32° F. when the sealed container suitable for administering an injectable unit dose is an ampul. This composition will also remain stable down to temperatures of 32° F. in vials which are closed with the following rubber closures washed according to standard sodium phosphate washing procedures known in the art:

1. Nitrile—Butadiene rubber
2. Halo Butadiene rubber
3. Any rubber closure which is coated with a fluorinated hydrocarbon polymer.

Nitrile—Butadiene rubber closure means rubber closures with a Nitrile—Butadiene elastomer reinforced with an inert mineral and cured with organic peroxide (such as West 2212).

Halo Butadiene rubber closure means rubber closures with a Halo Butadiene elastomer reinforced with an inert mineral and cured with phenolic resin (such as West 703/VII)

Fluorinated hydrocarbon polymer means any composition containing fluorinated hydrocarbon polymers and used as a coating material.

All West products are manufactured by West Company, Phoenixville, Penna. 19469

The resulting composition of 5FU represents a significant improvement over the current production formulas for increased resistance to precipitation.

The present invention will be further described in connection with the following Example which is set forth for the purposes of illustration only.

EXAMPLE I

West pH 703/VII or West 2212 rubber closures manufactured by West Company are washed according to the following procedure.

1. place rubber closures to be washed in a clean, stainless steel pot or glass receptacle. Cover closures with a 1% solution of tetrasodium pyrophosphate in distilled water.
2. autoclave container for ½ hour at 121° C.
3. Decant the liquid from the closures while still hot and then thoroughly rinse the closures with distilled water while agitating.
4. Immerse the closures in distilled water and autoclave for ½ hour at 121° C.
5 Repeat steps 3 and 4.

6. Inspect rinse water for clarity. If the rinse water is not clear, repeat the autoclaving with distilled water until the decanted water appears clear.

7. Sterilize washed stoppers by autoclaving in suitable breathable containers (e.g. autoclave bags) at 121° C. for 45 minutes. A drying cycle of at least 5 minutes should be used at the end of this sterilization to assure dryness of the sterile closure. Closures should be used within 48 hours of sterilization.

The 5FU composition is prepared by beginning with a 5FU solution manufactured according to current production methods known to one skilled in this art. This solution is then brought to a pH of 9.1 to 9.3 with sodium hydroxide. The volume is adjusted with water so that the final concentration of 5FU is 50 mg/ml.

The composition is then dispensed into vials which are sealed with the washed rubber closures.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

I claim:

1. A composition comprising a solution of 5-fluorouracil at a concentration of 50 mg/ml and sodium hydroxide present in an amount such that the pH of the composition is about 9.2, said composition stored in vials sealed with a sodium phosphate washed rubber closure selected from the group consisting of nitrile-butadiene rubber, halo butadiene rubber and any rubber closure which is coated with a fluorinated hydrocarbon polymer.

2. The composition of claim 1 wherein the sodium phosphate washed rubber closure in nitrile-butadiene rubber.

3. A method for the manufacture of a vial formulation of a 5-fluorouracil composition stable down to 32° F. comprising the steps of:

(a) adding a base to 5-fluorouracil to form a solution, the base being added in a sufficient amount so that the solution has a pH of about 9.2;

(b) adding water to the solution in an amount to obtain a desired concentration of 5-fluorouracil in the solution;

(c) placing the solution containing the desired concentration of 5-fluorouracil in vials; and (d) sealing the vials with a rubber closure subjected to a sodium phosphate wash which is selected from the group consisting of nitrile butadiene rubber, halo butadiene rubber, and a rubber closure which is coated with a fluorinated hydrocarbon polymer.

4. The method of claim 3 wherein concentration of 5-fluorouracil is 50 mg/ml.

5. The method of claim 4 wherein the base is sodium hydroxide.

6. The method of claim 5 wherein the sodium phosphate wash comprises the steps of:

(a) placing the rubber closures in a clean stainless steel pot or glass receptacle and covering them with a 1% solution of tetrasodium pyrophosphate in distilled water;

(b) autoclaving the container for ½ hour at 121° C.;

(c) decanting the liquid from the closures while still hot and then thoroughly rinsing the closures with distilled water while agitating;

(d) immersing the closures in distilled water and autoclaving for ½ hour at 121° C.;

(e) repeating steps 3 and 4 until the rinse water appears clear;

(f) sterilizing the washed closures by autoclaving in a suitable breathable container at 121° C. for 45 minutes;

(g) drying at least 5 minutes to assure dryness of the closure; and (h) using said closure within 48 hours of washing.

7. The method of claim 6 wherein the rubber closure subjected to the sodium phosphate wash is nitrile-butadiene rubber.

* * * * *